(12) United States Patent
Goldowsky

(10) Patent No.: US 6,716,157 B2
(45) Date of Patent: Apr. 6, 2004

(54) MAGNETIC SUSPENSION BLOOD PUMP

(76) Inventor: Michael P. Goldowsky, c/o Gold Medical Technologies, Inc. Westchester Medical Center, Elmwood Hall, Valhalla, NY (US) 10595

( * ) Notice: Subject to any disclaimer, the term of this patent is extended or adjusted under 35 U.S.C. 154(b) by 217 days.

(21) Appl. No.: 10/084,017

(22) Filed: Feb. 28, 2002

(65) Prior Publication Data

US 2003/0163019 A1 Aug. 28, 2003

(51) Int. Cl.$^7$ .................................................. A61M 1/12
(52) U.S. Cl. ....................................... 600/16; 623/3.14
(58) Field of Search .................... 600/16–18; 623/3.13, 623/3.14

(56) References Cited

U.S. PATENT DOCUMENTS 5,928,131 A * 7/1999 Prem ........................... 600/16
6,527,699 B1 * 3/2003 Goldowsky ................... 600/16

OTHER PUBLICATIONS

International PCT No. PCT/US00/15240, Filed Jun. 2, 2000—Inventor: Michael P. Goldowsky.
USA National PCT SN 09/980,264, Filed Nov. 27, 2001—Inventor: Michael P. Goldowsky.

* cited by examiner

Primary Examiner—Jeffrey R. Jastrzab
(74) Attorney, Agent, or Firm—Stanley J. Yavner

(57) ABSTRACT

An implantable magnetic suspension blood pump having a rotor magnetically suspended and having blood flow gaps at the axial ends of the rotor so that blood in the gaps is washed out by flow in a conduit along the axis of the rotor connecting the fluid gaps. The blood pump impeller includes main and secondary blades, an exit diffuser uses a plurality of low divergence blades wrapped circumferentially around the pump axis, and concentric cones are used at the pump outlet, all to eliminate flow separation. The trailing edges of all blades are limited to an included angle of fifteen degrees, also to eliminate flow separation.

17 Claims, 7 Drawing Sheets

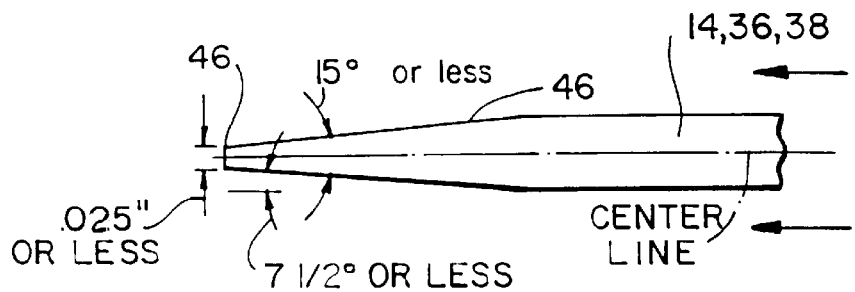
FIG. 5
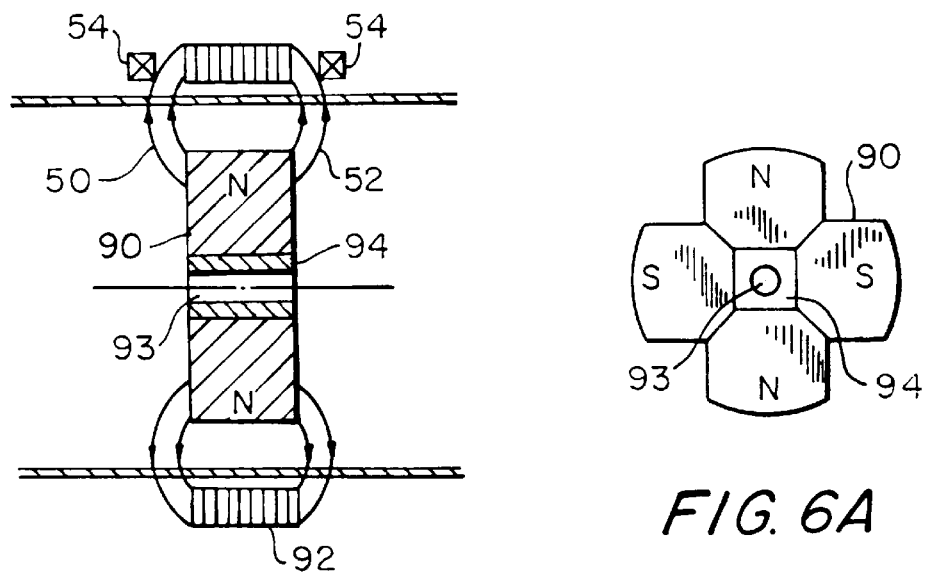
FIG. 6
FIG. 6A

MAGNETIC SUSPENSION BLOOD PUMP

FIELD OF THE INVENTION

This invention relates to blood pumps which are implanted into the chest of humans and are used to assist blood pumping in the hearts of such humans. More specifically, the present invention relates to those pumps which use magnetic suspensions or non-contacting bearings and which improve on the ability to wash out the bearing gaps for such pumps.

BACKGROUND OF THE INVENTION

As stated in my previous patent application (International Application No. PCT/US00/15240, filed on Jun. 2, 2000, Michael P. Goldowsky, Inventor), the then latest technology for assisting the heart involved implantable turbo blood pumps. These were usually axial flow configurations, centrifical configurations, and mixed flow types. Whichever form was used they employed high-speed rotary impellers, and most used hard-contact journal bearings to support the rotor. However, such bearings were prone to cause blood damage and thrombosis. Those contact-bearing problems have been eliminated by the use of magnetic bearings, which are non-contact bearings, to produce results with minimal blood damage, since magnetic bearing clearances are kept large to thereby reduce shear stress in the blood. Nevertheless, the requirement of thoroughly washing out all of the bearing clearances with fresh blood still must be enhanced to essentially eliminate the possibility of forming or enabling thrombus.

In my previous patent application, an improved alternative structure was set forth to eliminate thrombus formation at the bearings, by enabling bearing washout under minimal flow conditions through the pump. A magnetic bearing geometry was presented to easily washout the bearing gaps with fresh blood flow to prevent areas of stasis. The magnetic bearing was of a similar size and used an active coil and magnetic geometry requiring low power, approaching zero to sustain axial loads. Furthermore, the undesirable condition of reverse flow through the pump under pulsatile flow conditions was eliminated by the magnetic bearing monitoring pump differential pressure.

The present invention further improves bearing washout, provides compensating for control system failure, and minimizes flow separation by improving upon the various component geometries for the pump. Still further, the sensor for the magnetic bearing position is improved in the present invention by providing a new sensor structure. In addition to improving the geometry for blood in the pump, the present invention also improves the structure for packaging the electronics for the system. Additionally, the blood entering the pump is less prone to thrombosis by eliminating a separate inlet line connection. This is a significant improvement for the pump configuration and structure for implantation adjacent the heart or inside the left ventricle.

OBJECTS AND SUMMARY OF THE INVENTION

Accordingly, a primary object of the present invention is to use the large pressure difference existing across the impeller of human heart implantable blood pumps that employ magnetic bearings, to thoroughly wash out the bearing gaps for such pumps;

A further object of the present invention is to otherwise provide an implantable pump, using magnetic bearings, which avoids the formation or the enabling of thrombus;

A still further object of the present invention is to provide a structure for such devices which enables the thorough washout of all bearing clearances;

It is another object of the invention to provide a structure in such devices which improve the pump operation with back-up auxiliary mechanical bearings by means of touchdown pins thereon;

A primary additional object of the invention is to minimize or eliminate flow separation in such a device;

Another object of the present invention is to provide axial position-sensing for the magnetic bearings of such a device; and Yet another object of the present invention is to provide electronic reliability enhancement in an implantable pump by locating the electronics of such a device within the pump structure.

These and other objects of the present invention are provided in an implantable pump which features a pump impeller having a high pressure at the impeller outlet and a small suction at the impeller inlet, the difference in pressure causing blood to flow radially inwardly at the outlet bearing gap positioned at the impeller outlet. A central hole is provided in the rotor, through which the inwardly flowing blood passes, to flow radially outwardly at the inlet bearing gap. This creates continuous washout with fresh blood in both bearing gaps to eliminate thrombosis. The series flow resistance of the washout path, and therefore the flow rate, is varied by changing any of a number of component dimensions which allows maximum magnetic bearing design flexibility. An independent component dimension for example is the diameter of the hole in the rotor. Furthermore, there are two stationary conical touchdown pins, one at each end of the rotor. The radial clearances of these touchdown pins are in part chosen to obtain optimum blood velocities for washout. If velocity is too high, turbulence may cause hemolysis, whereas a velocity that is too low does not accomplish full washout, thereby leading to thrombosis.

The preferred conical touchdown pins contribute to the formation of a touchdown bearing, also including a matching conical pocket in the rotor, thereby to form, with the pin, a thrust-bearing to hold the axial load. The washout flow goes over the conical pins. To eliminate a potential stagnation point at the tip of the pins, the tip of the cone of the pin is located slightly off-axis, or an angled small flat, typically 20 degrees with a flat major axis of about three-quarters of a millimeter, is used. With the rotor rotating at upwards of 10,000 rpm, the flow is swirled on the surface of the flat, so stagnation cannot occur. Also, the axial gaps of the pins with the rotor pocket are chosen to allow a maximum permitted axial displacement of the rotor, displacement falling within the liftoff current capability of the stator coils. If the passive radial shock load capability of such magnetic bearings is exceeded, the touchdown pins radially contact the rotor pockets before the outside diameter of the rotor touches the housing.

The components of the pump are designed to largely eliminate flow separation on the transition surfaces traversed by the flow entering and leaving the impeller, through the annulus geometry. If flow separation on surfaces occurs, turbulence will result. In turn, hemolysis and thromboemboli will result. To eliminate such conditions on the rotating impeller, a secondary small blade is provided adjacent the inlet of each main blade of the impeller. This secondary blade limits the angle of flow divergence, preferably to a maximum of 15 degrees, on both blades as well as between the blades. Likewise, a special geometry is used in the exit diffuser and in the exit cones to limit the flow divergence angle to 15 degrees or less. The exit diffuser transitions the flow from a small cross sectional annulus area of the impeller to that of a larger flow area, thereby recovering velocity pressure. Indeed, eight blades are used in the exit diffuser, so that a small divergence angle exists between blades all along their length to eliminate flow separation. More blades could be used in the exit diffuser to reduce the angle of divergence further, but the blood contacting surface area of the diffuser will be undesirably increased. Also, the diffuser blades are wrapped circumferentially around the pump axis to create a longer effective blade length in a given axial distance, to further reduce the flow divergence angle and the number of blades required.

Flow separation is eliminated on pump surfaces in the transition of flow between the diffuser and the exit line conduit bore. This is accomplished by employing a tapered outlet cone, surrounded by an auxiliary cone outside this main cone. At the inlet to the cones, which is the diffuser exit, the flow is split, with a portion going between the outside surface of the auxiliary cone and the outlet line inside diameter, and the remainder passing between the two cones. Both flows have an included angle of divergence of 15 degrees or less to avoid flow separation on all surfaces. The effective axial length of the pump is not increased when a single long auxiliary cone is used, because this cone is located within the outlet line of the pump. Use of more than one nested auxiliary cone results in a proportionately shorter cone length for the same divergence angle.

Still further, the trailing edges of the impeller blades, the inlet blades, the cones, and the diffuser blades, are symmetrically terminated at an included angle of 15 degrees or less to minimize separation at the trailing edges. These edges are also made as thin as practicable, on the order of 0.005 inch.

A miniture eddycurrent position sensor is incorporated in one stator of the magnetic bearing, by using a small multi-turn coil located inside the bore of the magnetic bearing coil. The coil is operated at a high frequency to induce eddycurrents in a thin copper or other metallic target located at the end of the rotor. To avoid interference for the sensor coil, a thin hermetic window is placed in front of the coil and is of a non-metallic, non-conducting material. Likewise, the touchdown pin is non-metallic.

As to electronic packaging, the pump controller may be located in the hollow main exit cone. In this way controller heat is dissipated directly into the blood that flows over that cone and the need to implant a separate controller package with interconnections is eliminated. Due to the normally large implantable battery required for implantable pumps, the battery pack is located in a separate implantable package. Only two leads are necessary to connect this battery to the pump, when the pump electronics are located within or in adjacent contact with the pump, as one package.

Furthermore, design of the exit angle on the diffuser blades, to an exit angle of about 7 degrees relative to the pump axis, allows the outlet flow to swirl with a small tangential component forming a vortex to wash out the pump exit and avoid thrombus. This tangential velocity component of the main axial flow is kept small to minimize losses since it becomes dissipated as viscous heat.

The joint where an inlet line is connected to a blood pump is prone to poor washout and thrombosis formation. For the disclosed small pump the pump's preferred implantation location is adjacent the human heart, rather than inside the left ventricle. The need for a separate inlet line is avoided by extending the pump's titanium inlet tube into the left ventricle. A flare radius is employed to reduce turbulence in the flow entering the tube. The flare is positioned relatively close to the left ventricle inside wall to minimize stagnant areas of blood downstream of and surrounding the flare. This same configuration of flare radius is even usable with the pump implanted in the left ventricle.

Lastly, one or more auxiliary blades are added between the primary blades of the pump impeller in order to limit the divergence flow angle of the incoming flow to 15 degrees or less. In the disclosed design, these auxiliary blades are only necessary near the entrance to the main blades, since the divergence flow angle further along the blade is 15 degrees or less anyway. With other less steep helix angles for the primary blades, use of auxiliary blades over a greater length of the primary blades may be required to limit the divergence angle.

BRIEF DESCRIPTION OF THE DRAWINGS

These objects, features and advantages of the present invention are further detailed in the following description of a preferred, but nonetheless illustrative, embodiment, of the present invention, with reference to the accompanying drawings, wherein:

FIG. 5 shows the included angle for termination of trailing edges of impeller and inlet blades, the cones, and the diffuser blades, which results in minimum separation at the trailing edge;

FIG. 6 shows the use of magnetic field sensors to measure the axial magnetic field of the motor magnet; and the leakage fields are shown schematically;

FIG. 6A shows a right side view of the magnet of FIG. 6;

DETAILED DESCRIPTION OF THE INVENTION

Figure 1:
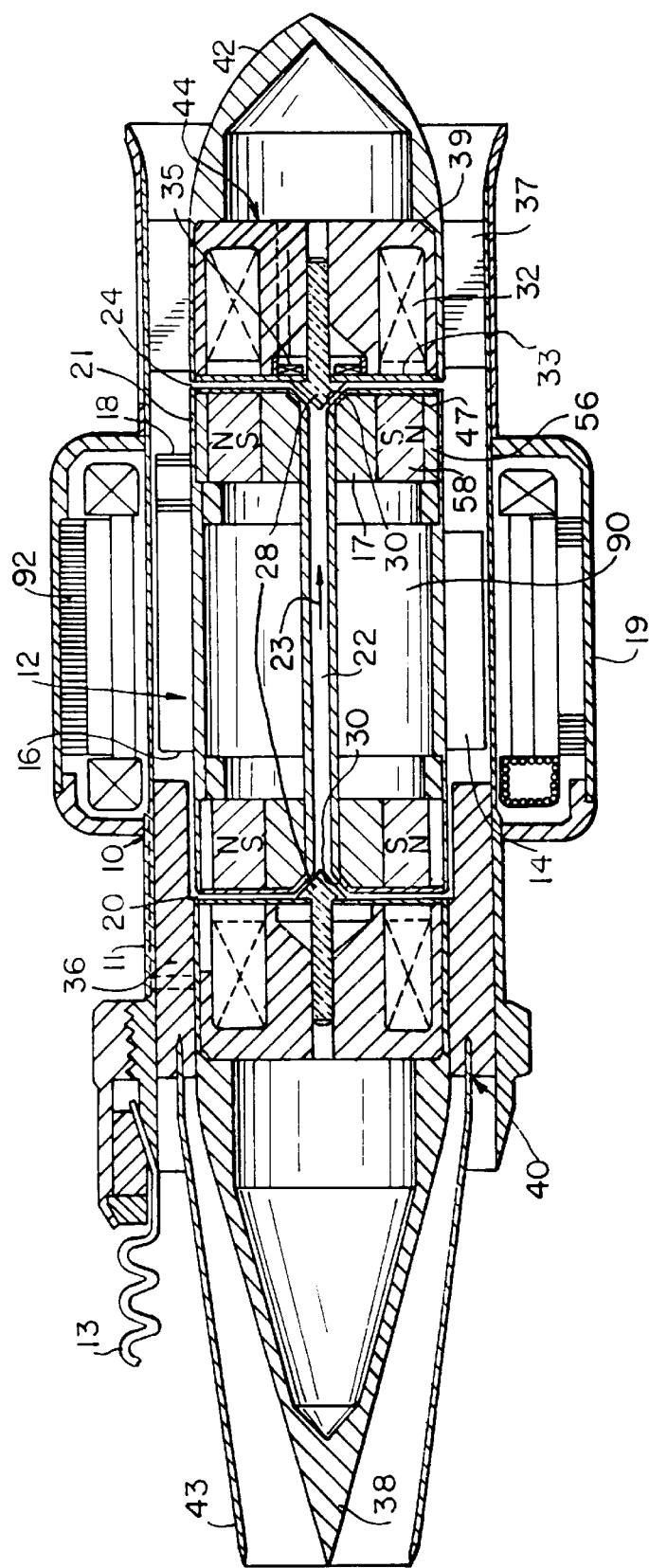
FIG. 1 is a sectional representation of a pump according to the present invention, showing details of the impeller, and the washout path provided.

FIG. 1, which is a sectional view for the purpose of clarity, represents an implantable pump generally designated 10, according to the present invention. The implantable pump includes motor housing 19, rotor 17, a pump housing 11, a pump impeller, generally designated 12, with the impeller having blades 14, and outlet 16 and inlet 18 portions. When the pump 10 is implanted, blood flows therethrough and ultimately exits at exit conduit 13, as well as by a main exit cone 38 and an auxiliary exit cone 43. The improved design uses one axial conduit 22 located proximate or on the center line of the pump rotor 17. This axial conduit connects the outlet bearing gap 20 and the inlet bearing gap 24 to allow blood flow to be conducted therebetween, in direction 23. A major advantage of this configuration is the utilization of the large pressure difference that exists across impeller 12 to vigorously wash out the bearing gaps. The total washout differential pressure across the two bearing gaps creates forced pressure washout of: the two bearing gaps, connecting tube and gaps over two pins 28, all in series. The centrifugal force of the spinning rotor creates equal centrifugal pressures in each bearing gap. These cancel one another since both are outward radially. Hence, centrifugal effects do not affect washout differential pressure. This also eliminates undersirable regurgitant flows in the gaps that could cause thrombus.

Figure 1A:
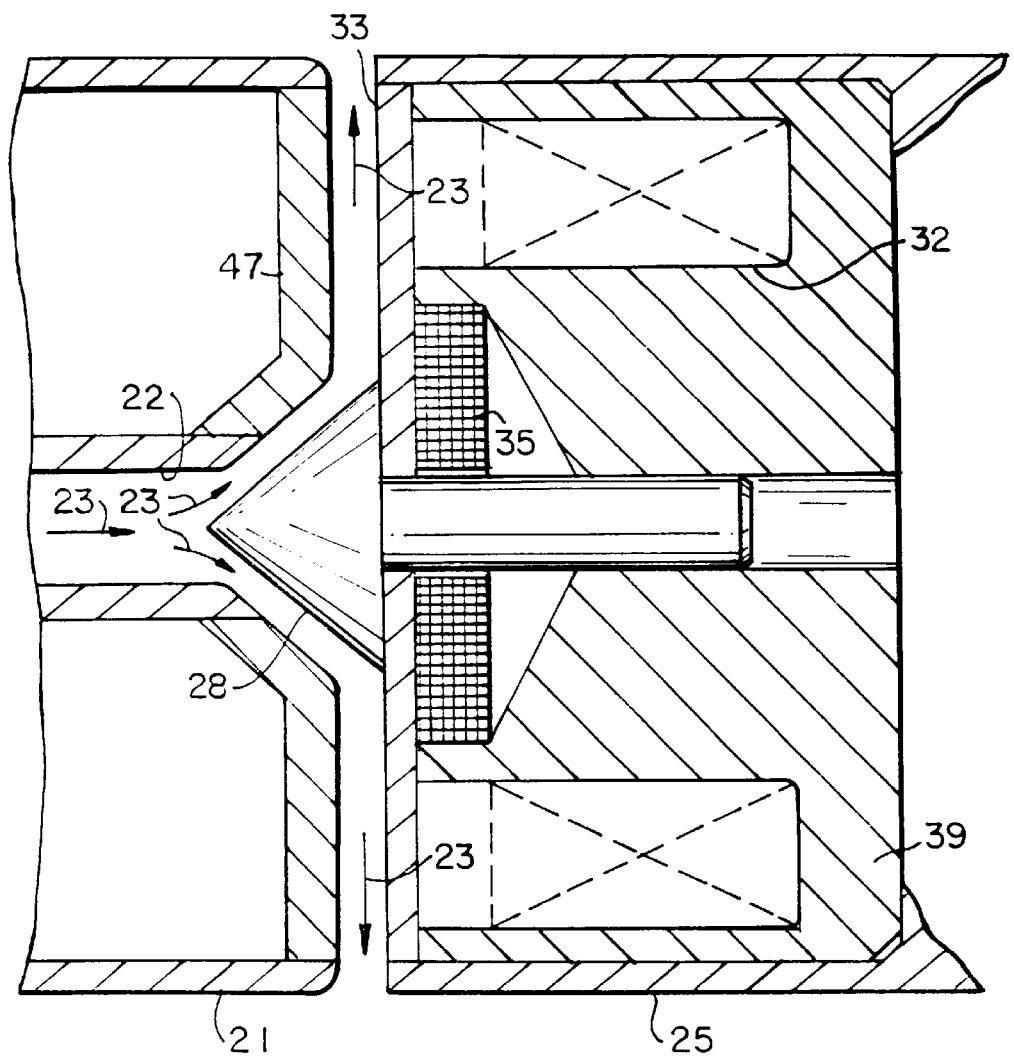
FIG. 1A is an enlarged fragmentary view of the inlet area of FIG. 1.

FIG. 1A is an enlarged, fragmentary view of the inlet area, generally 44, of FIG. 1, to show more clearly the structure proximate the pin radial gap clearance. FIG. 1A also shows the rotor titanium outer shell 21 and the titanium can 25 for the inlet structure.

Integrating touchdown pins 28 are used as back-up auxiliary mechanical bearings in the event the bearing axial electronic control system fails. Furthermore, electronic reliability enhancement is achieved by locating electronics within the pump itself. This eliminates separately implanted electronic packages and their interconnections.

The rotating impeller 12 greatly increases the static pressure in the blood for delivery to the patient. The impeller outlet 16 is at high pressure whereas a small suction exists at the impeller inlet 18. This differential pressure is typically 60 mm of mercury at a pump flow rate of 5 liters per minute and 100 mm of mercury pump outlet pressure. As shown in a cross-section of the pump in FIG. 1, this differential pressure causes blood to flow radially inward at the downstream bearing gap 20, which is positioned down-stream of the impeller outlet 16. The flow then passes through the central hole 22 (in a titanium or other blood compatible tube) in the rotor 17 as shown (in direction 23) and flows radially outward at the inlet bearing gap 24. This creates continuous washout with fresh blood in both bearing gaps 20, 24 which is essential to eliminate thrombosis. The series flow resistance of the path and hence wash out flow rate can be varied by changing the diameter of the hole 22 in the rotor, the radial clearance of the $Al_2O_3$ touchdown pins 28 and the bearing gap axial clearances, to obtain optimum blood velocities for washout. The turbulence associated with too high a velocity will cause hemolysis, whereas too low a velocity may not provide full washout of all areas of the passage, with resulting thrombosis.

In the event the magnetic bearing axial control system should fail, the rotor 17 will displace either to the right or to the left because it is axially unstable magnetically. The rotor will not fail radially because the bearing is passive in this direction. As shown in FIG. 1, two stationary conical touchdown pins 28 are located at each end of the rotor. In the event of control system failure a matching conical pocket 30 in the rotor mates with the pin as a thrust bearing to hold the axial load. Mechanical touching then occurs which is similar to bearings used in convential axial flow turbo-pumps, such as the Jarvik 2000 and Micromed. The washout flow previously mentioned also goes over the conical pins 28. To eliminate a potential stagnation point at the tip of the pins 28 (FIG. 2A), the tip can be located slightly off-axis (pin 28', FIGS. 2C and 2D) or an angled small flat as shown in the FIG. 2B pin 28" can be used. A typical flat angle is 20 degrees and flat major axis is ¾ millimeter. The fact that the rotor is rotating at 10,000 or more rpm, additionally swirls the flow on the surface of the flat 28a. The flat geometery changes circumferentially (unlike a conical symmetric tip FIG. 2A), so stagnation cannot occur as long as wash out flow exists, even without rotor rotation. If the pump totally fails, or is intentionally placed in a low rpm standby mode, tip stagnation will not occur.

In order to initially float the magnetic bearing with ease, the axial gaps of the pins 28 with the rotor pockets 30 are chosen to allow a maximum permitted axial displacement of the rotor. This maximum displacement falls within the lift-off current capability of the stator coils 32.

Figure 2A:
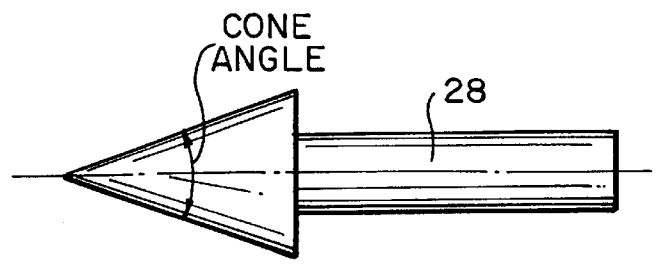
FIG. 2 is a representation of the touchdown pins, shown in various configurations in FIGS. 2A–2D, in order to explain pump operation, the action of the bearings thereof and otherwise.
Figure 2B:
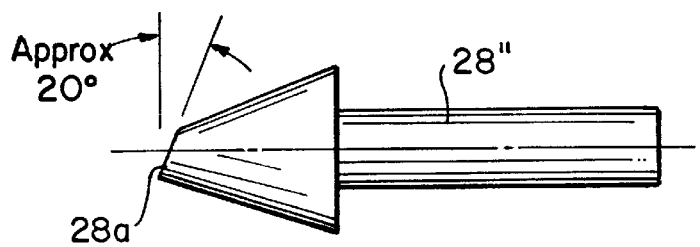
Figure 2C:
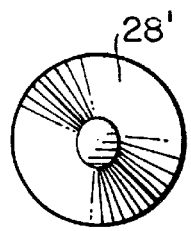
Figure 2D:
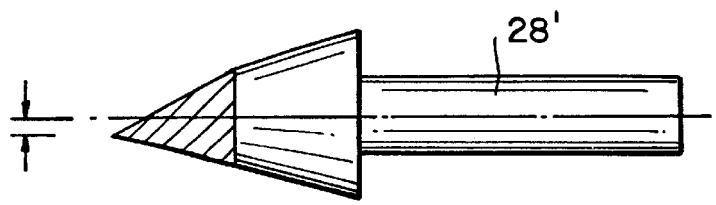

In pump operation, if the radial shock load capability of the magnetic bearings is exceeded, the pins are designed to radially contact the rotor pockets 30 before the rotor outside diameter touches the housing 11. The conical angle of the pin as shown in FIG. 2A is chosen to give the desired amount of rotor radial motion for a defined amount of rotor axial motion. This keeps the rotor outside diameter and magnetic bearing end faces from contacting the housing with imposed excessive radial and axial loads. The use of a conical pin, which has an independent cone angle, therefore allows satisfying two independent motions, namely the axial motion and radial motion touchdown constraints of the rotor.

A hard wear-resistant non-metallic pin such as aluminum oxide ceramic is preferred because a non-metallic pin will not electro-magnetically interfere with the operation of the eddycurrent position sensor coil 35 shown in FIG. 1 that surrounds the pin. The ceramic pin can be coated with soft carbon or preferably diamond-like carbon or titanium nitride for blood compatibility and wear-resistance. A titanium pin can be employed if the eddycurrent sensor is not used.

Figure 3:
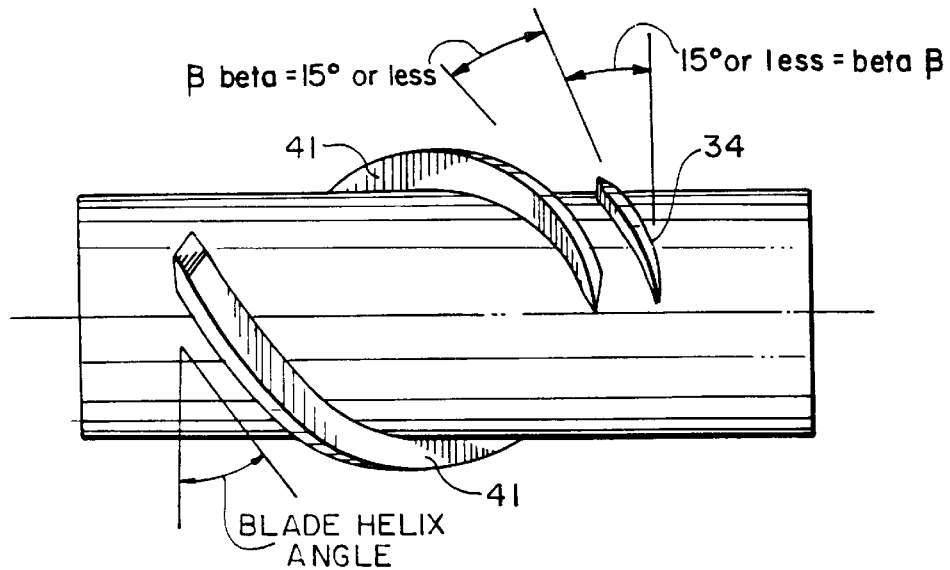
FIG. 3 represents the use of secondary small blades with the main blades of the pump impeller of the present invention.

In existing turbo blood pumps, as well as the one herein disclosed, the flow entering and leaving the impeller must transition from the inlet (or outlet) round tube geometry to that of the annulus geometry of the impeller. Flow separation in these transition regions will cause turbulence. Turbulence can result in hemolysis and thromboemboli existing in the downstream flow of the pump. Thromboemoli can lodge in the arterial system, brain or organs. This undesirable condition has been largely eliminated in the following components of the pump:

A secondary small blade 34 is used adjacent the inlet of each main blade 41 of the blood pump impeller as shown in FIG. 3. Adding one or more blades is done to limit the angle of flow divergence beta, to a maximum of 15 degrees between the two blades and between the secondary blade and the relative velocity of the incoming flow which is mainly tangential. An included angle of 15 degrees or smaller generally will not cause flow separation in a diverging passage. This same rule is used in the exit diffuser and exit cones discussed below. These two impeller secondary blades 34 need only subtend a small circumferential angular arc on the order of 45 degrees at the impeller inlet 18. In a preferred design, as shown in FIG. 3, there are two main blades 180 degrees apart labeled 41. Each subtends a circumferential angle of slightly more than 180 degrees so they angularly overlap as discussed in my former patent application. There are two secondary blades 34 (only one shown) which subtend 50 degrees, one for each primary blade. Short blades are used to minimize the amount of blade surface area in contact with the blood.

The exit diffuser 40 transitions the flow from a small cross-section annulus area of the impeller to a larger flow area, thereby recovering velocity pressure.

Figure 4:
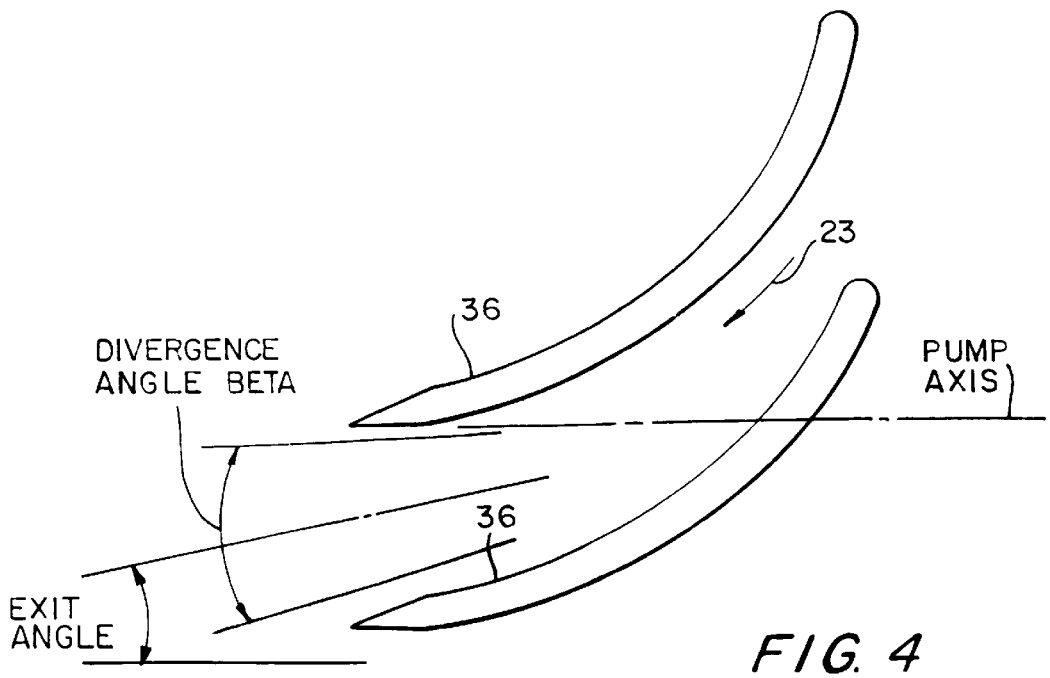
FIG. 4 shows the exit diffuser blades presenting a divergence angle beta for flow with a short axial length of diffuser blades, and yet a long enough wrap around blade length to avoid the drawbacks discussed herein.

The number of blades used in the exit diffuser (generally, 40) determines the local maximum divergence angle beta existing between diffuser blades 36 along the length of the blades. Limiting this included angle to about 15 degrees or less will eliminate flow separation as shown in FIG. 4. In the present design, this is accomplished with eight blades. An even smaller beta angle will result with the use of more blades, but this increases the blood contacting surface area of the pump, which is not desirable. In order to reduce the axial length of the diffuser blades which is important in keeping the axial length of the turbo-pump small, the blade 36 is wrapped helically around the pump axis. This creates a longer blade length in a given axial distance. A longer blade desirably reduces the flow divergence angle and number of blades required. The preferred eight blade design wraps the blade 36 about 90 degrees around the pump axis.

My previous patent application used a tapered outlet or semi-spherical cone to transition the flow from the impeller annulus to the exit line conduit bore. Existing pumps use a sphere or other geometry. In order to eliminate flow separation on this transition surface, the divergence angle beta, seen everywhere by the flow, should be limited to 15 degrees or less. This is not the case in existing pumps or in my previous patent application. The improvement herein uses an auxiliary cone 43 outside the main cone (which is on the center line of the pump) as shown in the FIG. 1. At the inlet to the cones (the diffuser exit), the flow is split up. Some goes between the outside surface of the auxiliary cone 43 and the exit conduit 13 inside diameter while the remainder passes between the two cones. Both flows have an included angle of divergence of only 15 degrees in FIG. 1, so no separation should occur on the cone surfaces or on the exit conduit inside diameter. One or more auxiliary cones 43 may be used. The more cones used, the smaller the divergence angle beta and the shorter the axial length required for the cones. The present use of one auxiliary cone and a main exit cone 38 creates an acceptable axial length of 1.0". This axial length is not a major constraint because the cones are located in the outlet line and the effective implanted axial length of the pump is not increased.

The trailing edges 46 of: the impeller blades 14, the inlet blades, the cone 43 and the diffuser blades 36, are preferably symmetrically terminated at an included angle of 15 degrees or less, as shown in FIG. 5. The symmetry gives an angle of 7-½ degrees relative to the blade center line as shown. This results in minimal separation at the trailing edge. The trailing edge 46 is also made sharp with a 0.003 of an inch typical flat or radius. This flat may vary from very sharp to 0.025 inch.

An eddycurrent position sensor coil 35 may be incorporated in one stator 39 of the magnetic bearing as shown in FIG. 1 by using a small diameter multi-turn coil 35. The coil is operated at a high frequency of about 1 megahertz in order to induce eddycurrents in a thin copper or metallic target window 47 located at the end of the rotor (at the rotor cap). The copper or other high electrical conductivity target window 47 can be carbon coated for blood compatibility. In order not to interfere with the performance of the sensor coil, the thin hermetic window 33 in front of sensor coil 35 as well as the touchdown pin 28, is made non-metallic. A preferred material is aluminum oxide. Use of a non-metal window and pin allows the electromagnetic field produced by the coil to pass through unimpeded to the sensed target. It should also be noted, for purposes of complete description, that FIG. 1 also shows a representation for stationary inlet blade 37. Also, the outer fringe ring 56 of the rotor's magnetic bearing is shown on FIG. 1.

If a thin metal window were used such as titanium, the coil frequency would have to be substantially reduced in order to penetrate the titanium. This would allow the surrounding magnetic material existing in the magnetic bearing to create its own eddycurrents and an undesirable cross-coupled target signal will result.

In a preferred position sensor embodiment, a thin titanium window 33, for blood comparability, is used to hermetically seal the magnetic bearing stator. No eddycurrent sensor coil is used. Small Hall sensors 54, or other type magnetic field sensors, are located outside the pump housing 11. They measure the axial magnetic field that emanates from the bearing and motor magnets in the rotor. The symmetric leakage fields 50, 52 are shown schematically in FIG. 6.

Axial motion of the rotor changes the magnitude of the axial component of the fields at Hall sensors 54. The leakage magnetic fields 50, 52 produced outside of the motor stator laminations 92, are produced by both the rotary motor's permanent magnet 90 and the magnetic bearing magnets 58.

Two Hall effect sensors 54 are located at each end of the motor stator laminations 92. They measure the strong leakage magnetic fields 50, 52 emanating from the rotor, as shown in FIG. 6. The difference signal of Hall sensors 54 is used. Due to the symmetry of fields 50, 52, the difference signal is zero when the motor magnet is centered between them. Axial displacement of the rotor increases one signal and decreases the other, so their difference is double the change obtained using one sensor. Also, their large DC levels cancel using a differential signal. This cancellation is required to obtain a large signal to noise ratio.

A constant leakage field is produced by the rear edge of the rotor's magnetic bearing magnets at respective Hall sensors 54. This adds to the motor magnet leakage field. Both leakage fields axially move together with rotor axial displacement. The differential axial fields may be sensed by sensors 54 to obtain axial displacement of the rotor. This axial signal is insensitive to rotor radial displacement, thereby eliminating undesirable cross-talk.

Because the brushless DC motor armature magnet has alternating north/south radial poles, each Hall effect signal will be alternating AC when the rotor rotates. Their difference amplitude varies with rotor axial position. At a rotor speed of 12,000 rpm the AC frequency obtained with the four pole motor magnet shown in FIG. 6A is sufficiently high (400 HZ) to provide the fast frequency response required for control of the magnetic bearing.

The motor magnet assembly has a soft iron core 94 to conduct magnetic flux. Core 94 has a central hole 93 to allow passage of titanium tube 22 used for flow of blood.

The electronics associated with a Hall Sensor or other solid state magnetic field sensor, such as magneto resistors, is substantially simpler, of lower cost and is more reliable than eddycurrent or coil inductance sensors. Redundancy is also provided using multiple Hall Sensors around the periphery of the motor.

Implantable blood pumps typically use a separate implantable battery for back-up power and a separate implantable electronics module. The separate electronics module is undesirable in that electrical interconnect leads or connectors interfacing to the pump are required. They can break or corrode and they decrease system reliability. It would be an improvement to reduce or eliminate electrical interconnection leads as well as the need to implant a separate electronic controller. The fewer the number of implanted parts, the less the chance for infection as well. This is very desirable for a long term use pump or for use in infants where implantation space is limited.

As shown in FIG. 1, the space taken by the inlet and outlet cones 42, 38 can be used to good advantage for packaging all or part of the pump electronics. These structures are made hollow for this purpose which also saves weight. By integrating the motor commutation circuits in the inlet cone 42 for example, all motor lead connections are internal to the pump and external leads and connectors are eliminated. By locating the pump controller in the hollow main exit cone 38, a larger exit cone loses its disadvantage since a separate controller package has been eliminated along with its interconnects. Controller heat is also desirably dissipated directly into the blood that flows over the cone.

Since the implantable battery is generally larger than this mini pump, the battery will normally require a separate implantable package. Only two leads need be used to transfer battery power to the pump when the pump electronics is located within or adjacent the pump. This is a vast improvement over current turbo pump systems that require many leads and connectors.

Existing axial flow turbo blood pumps or even turbo centrifugal blood pumps, expel blood into the outlet line colinear along the axis of the outlet line. This is good from an efficiency point of view because no energy is dissipated tangentially. However, of greater importance than maximizing efficiency is to insure against thrombosis formation at the point of attachment to the pump of the outlet line. This joint is susceptible to poor washout due to the unavoidable imperfect mating of the outlet line and the pump tube.

The natural heart guards against this at the aortic valve exit, where blood exists the heart and is pumped into the aorta of the body. The valve leaflets create a swirl in the flow or vortex with a tangential component. This swirl washes out the aorta entrance better than can be accomplished with pure axial flow.

The present invention mimics this by proper design of the exit angle on the diffuser blades shown in FIG. 4. By using a small tangential velocity component obtained by employing an exit angle of about 7.0 degrees relative to the pump axis, the outlet flow will swirl with a small tangential component to wash out the pump exit. This swirl proceeds some distance into the connecting line. This tangential velocity component of the main axial flow becomes dissipated as viscous heat. For a 7.0 degree angle, about 6% of the kinetic energy of the flow will be dissipated. This amounts to an even smaller fraction of the total flow enthalpy (or energy). Pump efficiency for exit angles up to about 15 degrees is minimally diminished.

The joint where a separate inlet line is connected to a blood pump is also prone to poor washout and thrombosis formation. The entire Jarvik 2000 axial flow turbo pump is located inside the left ventricle mainly for the purpose of not requiring a separate inlet line. Only an attached outlet line is used.

Figure 7:
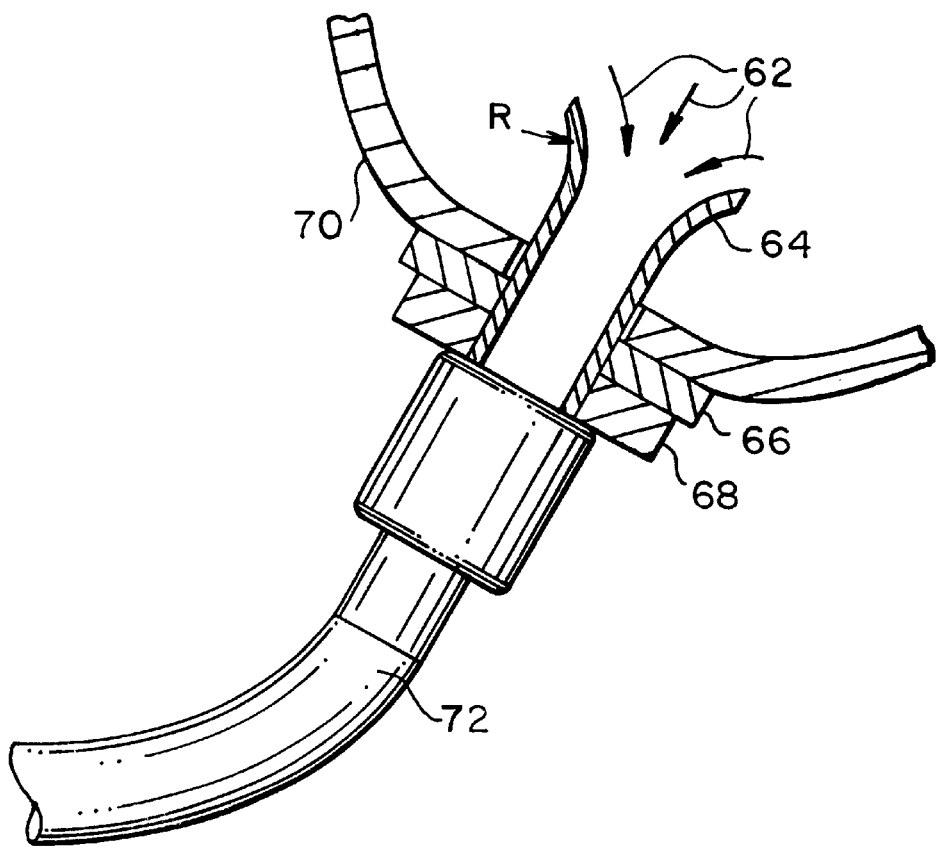
FIG. 7 indicates the extension for the pump's titanium inlet tube into the left ventricle of the human heart to withdraw blood.

The present invention is intended for implantation adjacent the heart, not inside the left ventricle; although it could be located there. A separate inlet line can be eliminated by extending the pump's titanium inlet tube 64 into the left ventricle to withdraw blood as shown in FIG. 7. A flare radius R is used to reduce turbulence in the flow entering the tube. The flare is positioned relatively close to the left ventricle inside wall in order to minimize blood stagnant areas downstream of and surrounding the flare. This same geometry can be used to withdraw blood from other areas of the heart as well.

FIG. 7 represents the blood flow by arrows 62 with the left ventricle wall of the heart 70 having a typical dacron cuff 66 sewn to the left ventricle. Dacron washer 68 is bonded to the pump. At implantation, it is sewn to the cuff 66, thereby supporting the blood pump and forming a leak-free interface. The pump outlet line 72 is also shown in FIG. 7. Thereby, the pump installation adjacent the heart, using the present invention, enables the elimination of a separate inlet line.

Figure 8:
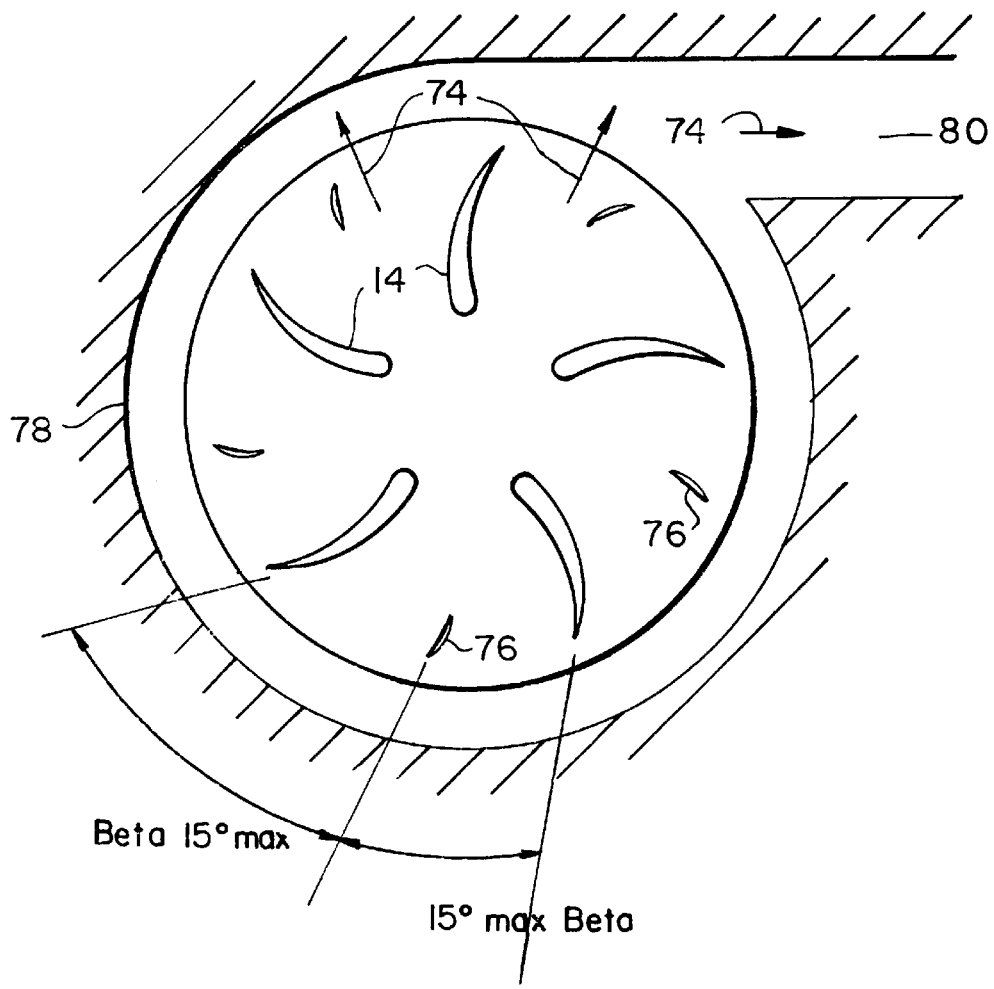
FIG. 8 shows the addition of one or more auxiliary blades between the primary blades of the impeller of a centrifugal blood pump to maximize performance as described herein.

FIG. 8 represents the impeller of a centrifugal blood pump with the addition of auxiliary blades 76 over a portion of the length of pump impeller blades 14, but only near the rotor outside diameter where they are required. These auxiliary blades limit the divergence flow angle beta to 15 degrees or less. Inside the auxiliary blade radius, beta may be 15 degrees or less, thereby eliminating the need for auxiliary blades there. With other configurations, it may be required that auxiliary blades be present only at the inner diameter area. If auxiliary blades are required all along the primary blade length, it may be that more primary blades would better be used, with the auxiliary blades not needed. If more primary blades are used, there is more blade surface area, which should be minimized in a blood pump. Accordingly, in order to provide the desired limit for beta, the blade total surface area is desirably minimized by using auxiliary blades as shown in FIG. 8.

The optimum configuration shown in FIG. 8 represents a centrifugal blood pump with outlet 80, with the impeller housed within a typical volute housing 78, and the flow direction shown by arrows 74.

The foregoing description shows the preferred and illustrative complete description of the present invention; but the limits thereof are only provided by the following claims:

What is claimed is:

1. A blood pump for human implantation to propel blood therethrough comprising:

a pump housing defining a pump axis, and inlet and outlet openings at opposite axial ends of said pump housing;

a rotor defining a rotor axis and opposing rotor axial ends;

magnetic suspension means within said pump housing at said rotor axial ends for magnetically suspending said rotor and defining fluid gaps between said rotor axial ends and said magnetic suspension means and substantially maintaining the stability of said rotor so that said rotor axis remains substantially coextensive with said pump axis during operation;

impeller means on said rotor operative to draw blood into said inlet opening and expel the blood through said outlet opening with rotation of said rotor;

drive means for rotating said rotor and impeller means thereby pumping blood; and blood washout means for continuously moving blood through said fluid gaps during rotation of said rotor to prevent formation of thrombus in said fluid gaps, including said rotor axis defining at least one conduit proximate said rotor axis and extending the length of said rotor axis for connecting said gaps to enable blood flow to be conducted therebetween.

2. A blood pump as defined in claim 1, wherein said pump comprises back-up auxiliary mechanical bearing means.

3. A blood pump as defined in claim 2, wherein said magnetic suspension means are bearings operated by an electronic control system and wherein said back-up auxiliary mechanical bearing means comprises a generally cylindrical touchdown pin at each end of said rotor, and a pocket to form with said pins thrust-bearings to hold the axial load, with said flow of blood being over said pins, and said back-up auxiliary mechanical bearing means being used in the event said bearing electronic control system fails.

4. A blood pump as defined in claim 3, wherein said touchdown pins each have a conical tip.

5. A blood pump as defined in claim 4, wherein the conical tips of said pins are located slightly off axis, with respect to said pin axis.

6. A blood pump as defined in claim 3, wherein said touchdown pins each have a spherical tip.

7. A blood pump as defined in claim 4, wherein said conical tips define a flat, angled with respect to the perpendicular to the axis of said pin.

8. A blood pump as defined in claim 1, wherein said impeller means comprises main blades, and secondary blades for said impeller are provided to limit the angle of flow divergence, to a maximum of 15 degrees relative to all blade surfaces.

9. A blood pump as defined in claim 1, wherein an inlet cone is located proximate said inlet opening and an exit cone and exit diffuser are located proximate said outlet opening, and each of said exit cone and said exit diffuser include means for eliminating flow separation.

10. A blood pump as defined in claim 9, wherein said means for eliminating flow separation limits the flow divergence angle to 15 degrees or less.

11. A blood pump as defined in claim 9, wherein said means for eliminating flow separation includes, for said exit diffuser, a plurality of blades, with each helically wrapped around the pump axis.

12. A blood pump as defined in claim 11, wherein said means for eliminating flow separation includes, as to said exit cone, an auxiliary cone outside of the exit cone, so that some of said blood flow passes between the two cones and some of said blood flow being split at said exit diffuser to flow over the outside surface of said auxiliary cone.

13. A blood pump as defined in claim 12, wherein a plurality of concentric auxiliary cones are included, with no more than a 15 degree flow divergence angle between all auxiliary cones, and elsewhere where flow occurs prior to exiting.

14. A blood pump as defined in claim 12, wherein pump electronics are used and located within said exit cone.

15. A blood pump as defined in claim 9, wherein pump electronics are used and located within said inlet cone.

16. A blood pump as defined in claim 1, wherein said pump defines a pump bore and said magnetic suspension means includes a stator, a thin window used to hermetically seal said stator, small magnetic field sensors located outside of said pump bore to measure the magnetic field that surrounds said pump rotor, said magnetic field sensors being adapted and arranged to reliably measure the differential leakage field surrounding said rotor which changes with rotor axial position.

17. A blood pump as defined in claim 16, wherein said thin window is titanium.

* * * * *